(12) United States Patent
Gorek et al.

(10) Patent No.: US 8,734,338 B2
(45) Date of Patent: May 27, 2014

(54) MINIMALLY INVASIVE RETRACTOR AND METHODS OF USE

(71) Applicant: K2M, Inc., Leesburg, VA (US)

(72) Inventors: Josef Gorek, Ross, CA (US); John Kostuik, Baltimore, MD (US); George Picetti, Granite Bay, CA (US); Kevin R. Strauss, Leesburg, VA (US); Michael Barrus, Ashburn, VA (US); Larry McClintock, Gore, VA (US); Richard W. Woods, Catonsville, MD (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/648,409

(22) Filed: Oct. 10, 2012

(65) Prior Publication Data

US 2013/0041228 A1 Feb. 14, 2013

Related U.S. Application Data

(60) Continuation of application No. 12/941,143, filed on Nov. 8, 2010, now Pat. No. 8,298,138, which is a division of application No. 11/528,223, filed on Sep. 26, 2006, now Pat. No. 7,846,093.

(60) Provisional application No. 60/720,670, filed on Sep. 26, 2005.

(51) Int. Cl.
*A61B 1/32* (2006.01)

(52) U.S. Cl.
USPC .......................................................... 600/232

(58) Field of Classification Search
USPC ............ 606/246, 264, 265, 279, 96, 99, 104, 606/86 A, 304; 600/201, 204, 206, 208, 600/210, 211, 213, 214
See application file for complete search history.

(56) References Cited

U.S. PATENT DOCUMENTS

| | | | |
|---|---|---|---|
| 3,129,706 | A | 4/1964 | Reynolds |
| 5,242,443 | A | 9/1993 | Kambin |
| 5,582,577 | A | 12/1996 | Lund |
| 5,685,826 | A | 11/1997 | Bonutti |
| 5,902,231 | A | 5/1999 | Foley et al. |
| 5,944,658 | A | 8/1999 | Koros et al. |
| 6,099,547 | A | 8/2000 | Gellman et al. |
| 6,187,000 | B1 | 2/2001 | Davison et al. |
| 6,200,322 | B1 | 3/2001 | Branch et al. |
| 6,206,826 | B1 | 3/2001 | Mathews et al. |
| 6,270,501 | B1 | 8/2001 | Freiberg et al. |
| 6,360,750 | B1 | 3/2002 | Gerber et al. |
| 6,530,926 | B1 | 3/2003 | Davison |
| 6,530,929 | B1 | 3/2003 | Justis et al. |
| 6,616,605 | B2 | 9/2003 | Wright |
| 6,743,206 | B1 | 6/2004 | Smith |

(Continued)

*Primary Examiner* — Pedro Philogene
*Assistant Examiner* — David Comstock
(74) *Attorney, Agent, or Firm* — Carter, DeLuca, Farrell & Schmidt, LLP

(57) ABSTRACT

A device, system and method for orthopedic spine surgery using a novel screw-based retractor, disclosed herein, that allows for access to the spine through a minimally or less invasive approach. The retractor device is designed to be coupled to a pedicle screw and then to have opposed arms of the retractor spread apart to open the wound proximally. The retractor is removed by pulling it out of the wound whereby the retractor is deformed to pass over the pedicle screw head. The retractor is intended to be made of a stiff plastic material, sterile packaged and disposable after one use. A system and method for using the retractor and performing a minimally invasive spine surgical procedure are also disclosed.

24 Claims, 19 Drawing Sheets

(56) References Cited

U.S. PATENT DOCUMENTS

| | | |
|---|---|---|
| 6,796,422 B1 | 9/2004 | Lu |
| 6,800,084 B2 | 10/2004 | Davison et al. |
| 6,802,844 B2 | 10/2004 | Ferree |
| 6,849,064 B2 | 2/2005 | Hamada |
| 6,929,606 B2 | 8/2005 | Ritland |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,083,621 B2 | 8/2006 | Shaolian et al. |
| 7,108,705 B2 | 9/2006 | Davison et al. |
| 7,144,393 B2 | 12/2006 | DiPoto et al. |
| 7,160,300 B2 | 1/2007 | Jackson |
| 7,166,107 B2 | 1/2007 | Anderson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,491,208 B2 | 2/2009 | Pond, Jr. et al. |
| 7,666,189 B2 | 2/2010 | Gerber et al. |
| 2003/0004401 A1 | 1/2003 | Ball |
| 2003/0191371 A1 | 10/2003 | Smith |
| 2004/0138662 A1 | 7/2004 | Landry et al. |
| 2005/0065517 A1 | 3/2005 | Chin |
| 2005/0131408 A1 | 6/2005 | Sicvol et al. |
| 2005/0165408 A1 | 7/2005 | Puno et al. |
| 2006/0074445 A1 | 4/2006 | Gerber et al. |
| 2006/0229614 A1 | 10/2006 | Foley et al. |
| 2006/0264962 A1 | 11/2006 | Chin et al. |
| 2007/0055247 A1 | 3/2007 | Jahng |
| 2007/0129731 A1 | 6/2007 | Sicvol et al. |
| 2007/0167954 A1 | 7/2007 | Sicvol et al. |

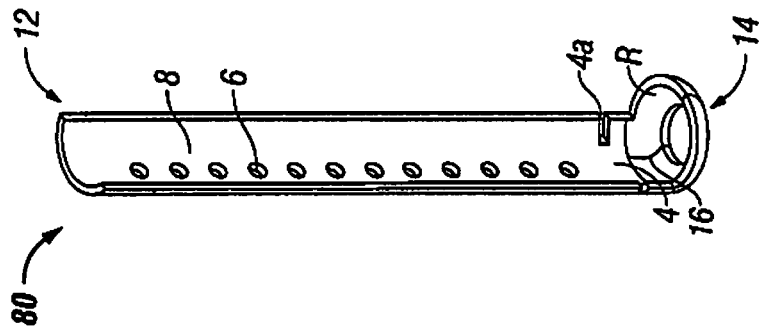
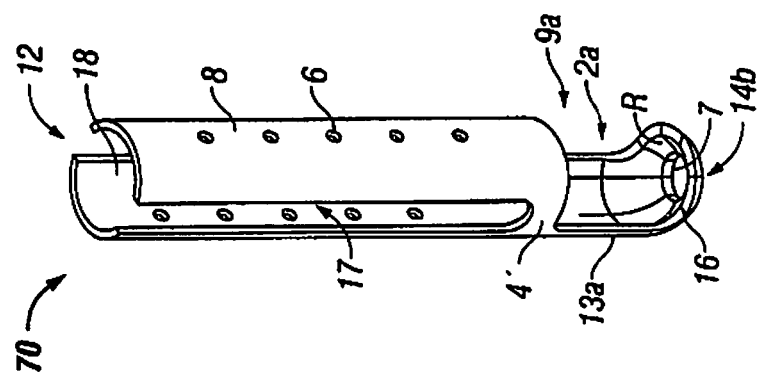
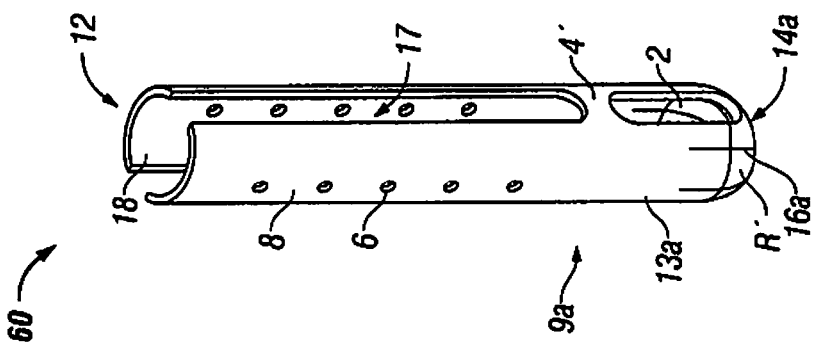

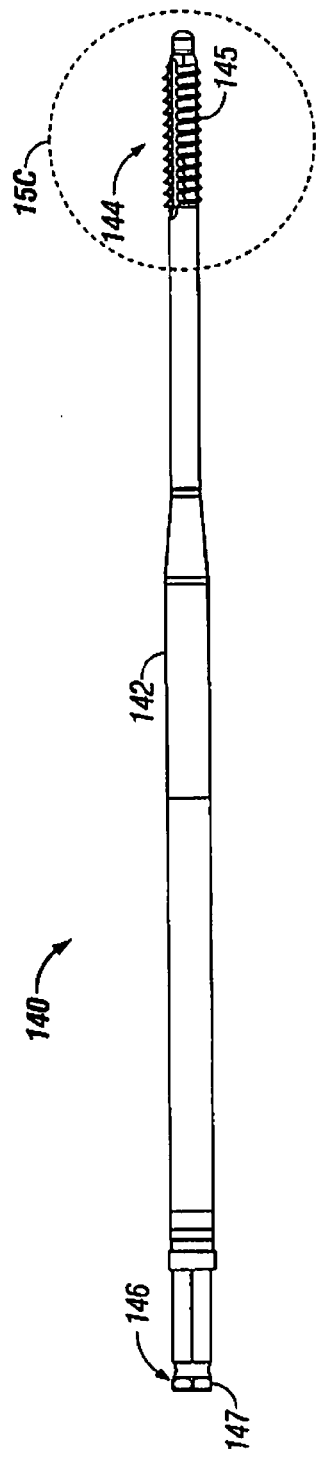
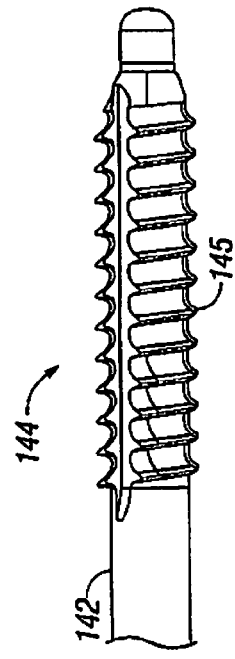
FIG. 15A
FIG. 15C
FIG. 15B

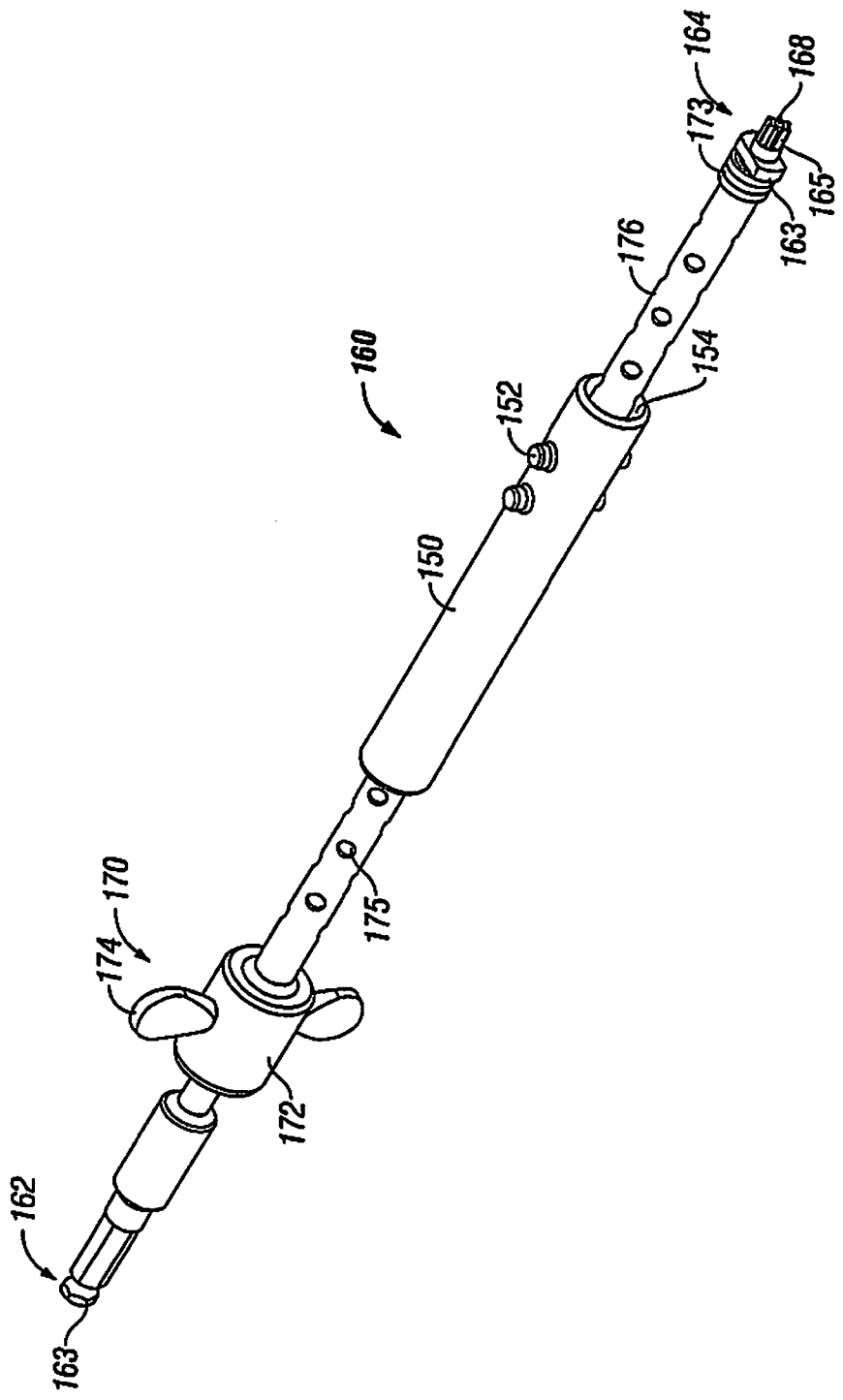

MINIMALLY INVASIVE RETRACTOR AND METHODS OF USE

CROSS-REFERENCE TO RELATED APPLICATIONS

This patent application is a continuation of U.S. application Ser. No. 12/941,143, filed on Nov. 8, 2010, which is a divisional of U.S. patent application Ser. No. 11/528,223, filed Sep. 26, 2006, now U.S. Pat. No. 7.846,093, which claims priority to U.S. Provisional Application Ser. No. 60/720,670, filed on Sep. 26, 2005, the contents of each of these prior applications are incorporated herein by reference in their entireties.

BACKGROUND

1. Field of the Invention

This invention relates generally to orthopaedic spine surgery and in particular to a minimally invasive retractor and methods for use in a minimally invasive surgical procedure.

2. Background of the Technology

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known in the prior art and can be modified to fit the contours of these small incisions, but they require manual manipulation to maintain a desired placement, thereby occupying one hand of the physician or requiring another person to assist the physician during the procedure. Typical retractors are also positioned into the soft tissue and are levered back to hold the wound open, frequently requiring re-positioning if they dislodge, obstruct the physician's view, or interfere with access to the surgical site.

In recent years, minimally invasive surgical approaches have been applied to orthopaedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e. liquid or gas) for distending tissue and creating working space for the surgeon. Surgery on the spine does not involve a capsule or space that can be so distended, instead involving multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. The difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e. as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly reduced post-operative pain, a shorter hospital stay, and a faster overall recovery.

Most spine implant procedures are open procedures, and while many manufacturers advertise a minimally invasive method, the procedure is typically not recommended for fusions and focuses on more common and accepted minimally invasive spine procedures such as kyphoplasty, vertebroplasty, and discectomy.

Medtronic Sofamor Danek's SEXTANT® is a true minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the setscrew. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT® only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding the issue completely for fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

The present disclosure relates to a device, a system, and a method for a screw-based retractor used in performing minimally invasive spine surgery. The retractor is removably attached to a pedicle bone screw that is used to guide the retractor into place and act as a point of fixation with respect to the patient. Multiple retractors may be used in conjunction with a single screw to allow retraction in multiple directions and multiple retractors may be used with multiple screws, respectively, during a single spine procedure. The retractor may be manufactured for a single use or can be sterilized and reused. Finally, the retractor may also act as a guide that will aid in the insertion of instruments and implants.

In its nominal position, the retractor will form a generally cylindrical tube with at least one retracting blade. Instrument holes are located perpendicular to the long axis of each retracting blade whereby a standard surgical instrument, such as a Gelpi Retractor, can be used to separate the blades to retract the skin and soft tissue and maintain the field of view. Yet, where the retractor is connected to the pedicle screw the retractor maintains a circular cross-section. Since the retractor is not permanently fixed but is removably attached to the pedicle screw, it is free to have polyaxial rotation allowing the surgeon greater wound access and freedom to operate. Furthermore, polyaxial rotation allows the retractor to expand medial-laterally as well as cephalad-caudally and any combination thereof. This freedom of movement proximally and non-rigid attachment distally decreases the need for retractor re-positioning during a procedure. Proximal stabilization of the retractor is possible when it is used in conjunction with a table-mounted retractor.

The minimally invasive retractor can be designed to flex proximal or distal to the pedicle screw head. In one embodiment, the retractor has a "living hinge" incorporated into the retractor's blade design. More than one living hinge can be incorporated to aid in bending along any portion of the blade's length.

The cross-section of the blade is a circular ring sector to provide additional stiffness. The geometry will force the blade to bend at the living hinge and still be able to retract the soft tissue pressed against it.

Minimally invasive retractors having a living hinge or a true hinge located may include at least one window that is aligned with the pedicle screw saddle and allows the insertion of instruments into the surgical site.

The distal tip of the minimally invasive retractor is bullet shaped to aid in insertion through the soft tissue to where it will seat against the pedicle. The distal tip will also have one or more relief features cut into it to aid in removing the retractor. Upon completion of the procedure, the retractor can be pulled straight out of the wound and the distal tip will expand or separate to pass over the screw and rod assembly. Advantageously, by positioning the distal tip of the retractor around the head of the screw adjacent the bone, the retractor retracts soft tissue from a point below the head of the screw, creating excellent visibility of the screw and surrounding tissue.

BRIEF DESCRIPTION OF THE DRAWINGS

Embodiments of the presently disclosed minimally invasive retractor are described herein with reference to the accompanying drawings, wherein:

FIG. 10 is a perspective view of a fourth embodiment of the presently disclosed minimally invasive retractor;

FIG. 11 is a perspective view of a fifth embodiment of the presently disclosed minimally invasive retractor;

FIG. 12 is a perspective view of a sixth embodiment of the presently disclosed minimally invasive retractor;

FIG. 15A is a side view of a cannulated bone screw tap;

FIG. 15B is a front elevational view of the bone screw tap of FIG. 15;

FIG. 15C is an enlarged side view of the detailed area "A" of FIG. 15;

FIG. 16 is a perspective view of a screw inserter having an anti-rotation sleeve;

DETAILED DESCRIPTION OF THE EMBODIMENTS

Figure 4:
FIG. 4 is a bottom view of the minimally invasive retractor of FIG. 2.

Embodiments of the presently disclosed minimally invasive retraction device will now be described in detail with reference to the drawings wherein like reference numerals identify similar or identical elements. In the drawings and in the description which follows, the term "proximal", as is traditional, will refer to the end of the minimally invasive retraction device which is closest to the operator while the term "distal" will refer to the end of the device which is furthest from the operator.

Figure 2:
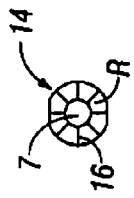
FIG. 2 is a bottom view of the minimally invasive retractor of FIG. 1.
Figure 1:
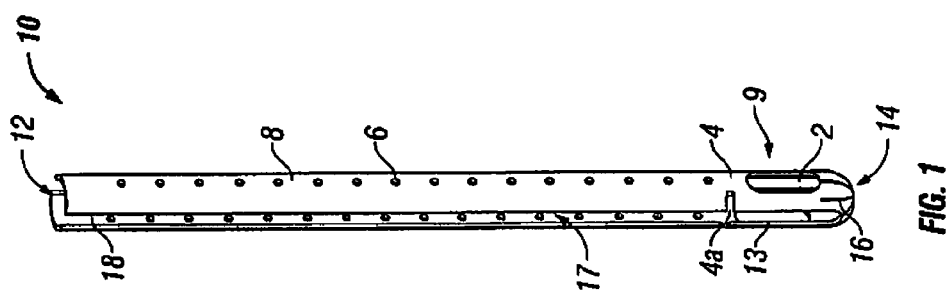
FIG. 1 is a perspective view of a minimally invasive retractor according to a first embodiment of the present disclosure.

Referring intially to FIGS. 1 and 2, a first embodiment of the presently disclosed minimally invasive retractor or retractor is illustrated and generally designated as 10. Retractor 10 includes an open proximal end 12 and a distal end 14. In addition, retractor 10 includes a pair of retractor blades 8 having a plurality of instrument holes 6 disposed on each of retractor blades 8. Instrument holes 6 are configured and dimensioned to cooperate with different surgical instruments as will be discussed in detail hereinafter. A distal region 9 of retractor 10 includes an opening 7 (FIG. 2), at least one slot or window 2, and a pair of arms 13 extending from distal end 14 to a flexible region or living hinge 4. Window 2 is sized and configured to receive instruments therethrough. Each retractor blade 8 is attached to living hinge 4 to define a substantially continuous elongate member. A pair of recesses 4a are formed between retractor blade 8 and arm 13 to define living hinge 4.

Distal end 14 further includes at least one relief region R (FIG. 2) defined by at least one slit 16 extending proximally from opening 7 (FIG. 2). Alternatively, slit 16 may originate at window 2 and extend distally towards opening 7. It is contemplated that other arrangements of relief structures may be used to define relief region R and these may exist between opening 7 and window 2. Each slit 16 is a weakened portion of distal end 14. It may be a score in the material, a perforated region in the material, or another structural arrangement allowing relief region R to be radially displaced away from the centerline of retractor 10 in response to applied forces as will be discussed in detail hereinafter. In addition, distal end 14 has a generally convex outer surface that facilitates insertion of retractor 10 through layers of body tissue.

Retractor blades 8 and arms 13 are generally arcuate structures that cooperate to define a substantially circular configuration for retractor 10. Each retractor blade 8 and each arm 13 have an arcuate configuration that is less than about 180° and are radially spaced apart to define a continuous slot 17 along a substantial portion of retractor 10. In addition, each retractor blade 8 and its corresponding arm 13 define a passage 18 that also extends substantially the entire length of retractor 10. Passage 18 is expandable, as will be discussed in detail hereinafter, for receiving a rod 3 (FIG. 9) therein. Retractor blades 8 and arms 13 define a substantially circular ring shape, thereby providing sufficient stiffness (i.e. rigidity) such that retractor blades 8 and arms 13 resist bending from the counter forces of the retracted tissues.

Opening 7 is located at distal end 14 of retractor 10 and is sized for receiving the shank of a threaded screw 40 (FIG. 20) therethrough, but inhibiting passage of a head 42 of screw 40 so as to support screw 40 at distal end 14 of retractor 10. The interior surface of distal end 14 has a generally concave spherical geometry that is adapted to mate with head 42 of pedicle screw 40 that is best seen in FIG. 11.

Retractor 10 is formed from a suitable biocompatible material having the desired physical properties. That is, retractor 10 is formed of a biocompatible, sterilizable material in a suitable configuration and thickness so as to be sufficiently rigid to be held on the screw when desired during insertion and a surgical procedure and to provide retraction of tissue, and yet is sufficiently bendable to be spread apart to provide retraction and to be forcibly removed from the screw as necessary and appropriate. It is contemplated that retractor 10 may be formed from polymers such as polypropylene, polyethylene, or polycarbonate. Additionally, retractor 10 may be formed from silicone, polyetheretherketone ("PEEK"), or another suitable material. Retractor blade 8 is bendable away from the centerline of retractor 10 in response to applied forces, wherein retractor blade 8 bends at living hinge 4. Bending retractor blade 8 away from the centerline (i.e. radially outwards) creates a larger opening through retractor 10 and also acts to retract the surrounding tissue at the selected surgical site. Installation and use of retractor 10 in surgical procedures will be discussed in detail hereinafter.

Figure 3:
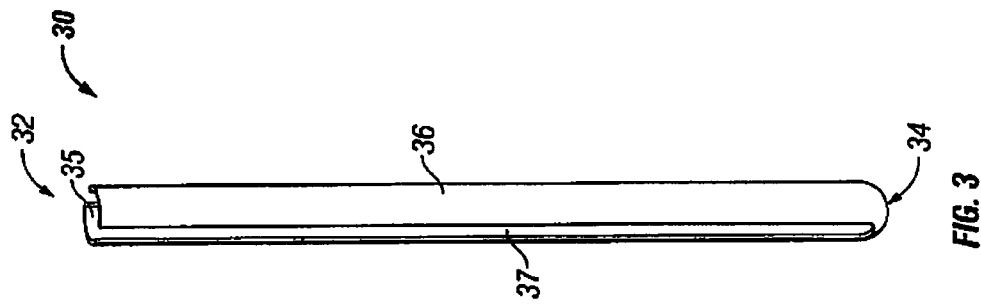
FIG. 3 is a perspective view of a minimally invasive retractor according to a second embodiment of the present disclosure.

Referring now to FIGS. 3 and 4, a second embodiment of the present disclosure is illustrated as retractor 30 having an open proximal end 32 and a distal end 34. Retractor 30 includes a pair of retractor blades 36. Similar to retractor 10, distal end 34 has an interior surface with a generally concave spherical geometry that is adapted to mate with the head of a pedicle screw and has a generally convex outer surface that facilitates insertion of retractor 30 through layers of body tissue. Additionally, retractor 30 includes an opening 7 (FIG. 4) that is substantially identical to opening 7 of retractor 10.

As in the previous embodiment, blades 36 have an arcuate configuration that is less than about 180° and are radially spaced apart to define a continuous slot 37 along a substantial portion of retractor 30. Additionally, retractor blades 36 define a passage 35 through retractor 30. In this embodiment, retractor blades 36 are also flexible, but bend radially outwards from a centerline of retractor 30 near relief regions R (FIG. 4). As in the previous embodiment, relief regions R are defined by slits 16 (shown as a pair of slits in FIG. 4) as previously discussed in connection with retractor 10. In this embodiment, retraction of tissue with retractor blades 36 utilizes manual manipulation of retractor blades 36 by the physician rather than using a surgical instrument in cooperation with instrument holes 6 of retractor 10 (FIG. 1). Removal of retractor 30 from the surgical site is accomplished by pulling retractor 30 proximally (i.e. away from the pedicle screw) and spreading or breaking distal end 34 along slits 16 such that relief regions R and retractor blades 36 separate from each other. As such, the physician can readily remove the two parts from the surgical site. Similar to passage 18 (FIG. 1), passage 36 is selectively expandable and contractible for receiving rod 3 therein.

Figure 7:
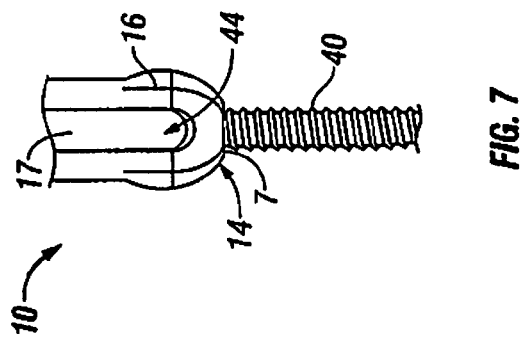
FIG. 7 is an enlarged side view of the detailed area "A" of FIG. 5.
Figure 6:
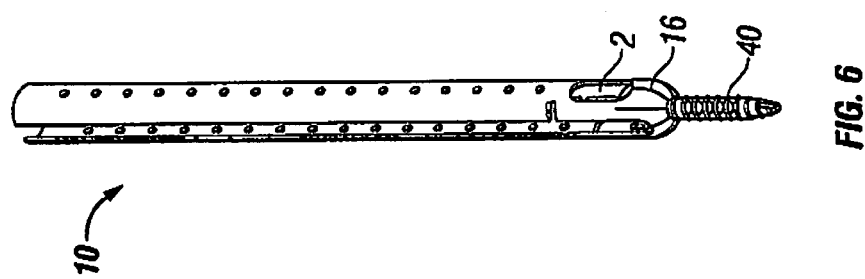
FIG. 6 is a perspective view of the minimally invasive retractor and screw assembly of FIG. 5.
Figure 5:
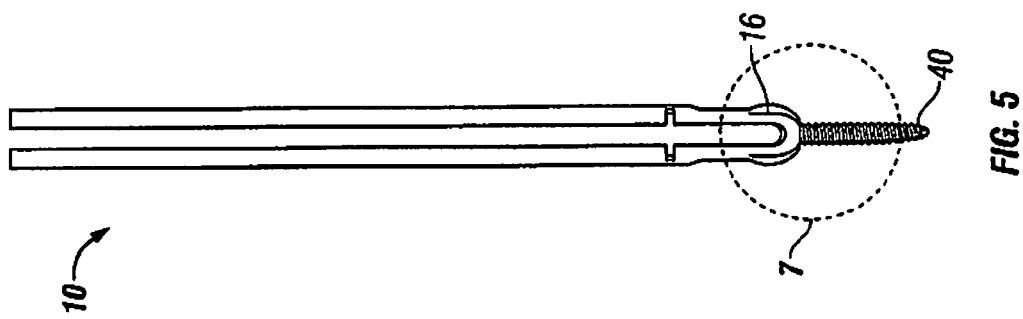
FIG. 5 is a side view of a minimally invasive retractor and screw assembly including the minimally invasive retractor of FIG. 1.
Figure 20A:
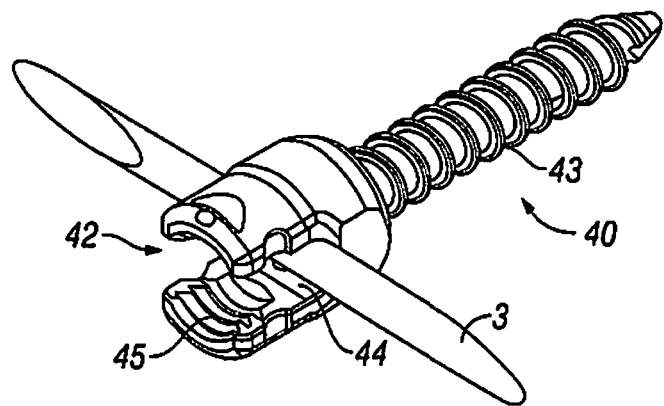
FIG. 20A is a perspective view of a cannulated screw showing a rod positioned in a rod receiving passage.

In FIGS. 5-7, retractor 10 is illustrated in an assembled condition with a pedicle screw 40. Pedicle screw 40 extends through opening 7 (FIG. 7) such that threads of pedicle screw 40 extend beyond distal end 14 (FIG. 7) for insertion into a target site in a bone (e.g. a vertebral body). As shown in the figures, when pedicle screw 40 is inserted in retractor 10, the head of pedicle screw 42 (FIG. 20) mates with the interior geometry of distal end 14. As shown, rod receiving passage 44 of pedicle screw 40 (FIG. 20) aligns with opening 17 between retractor blades 8 facilitating the insertion of rod 3 (FIG. 20)

into screw head 42. In addition, pedicle screw 40 is pivotable about the longitudinal axis of retractor 10 allowing retractor 10 to be attached in a first angular orientation with respect to the vertebral body, but pivotable about pedicle screw 40 increasing the amount of tissue that may be retracted using retractor 10.

Figure 9:
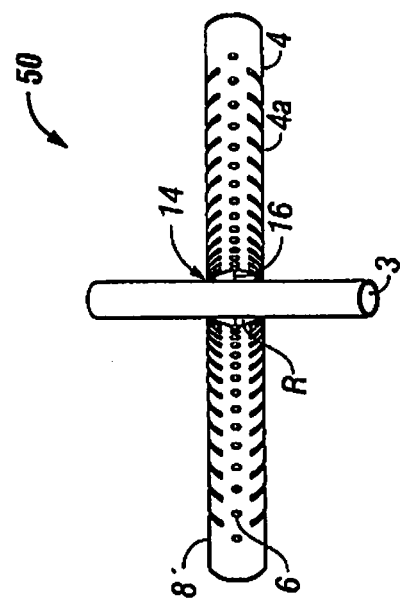
FIG. 9 is a top view of the minimally invasive retractor and screw assembly of FIG. 8 showing a rod extending through an expanded passage of the minimally invasive retractor.
Figure 8:
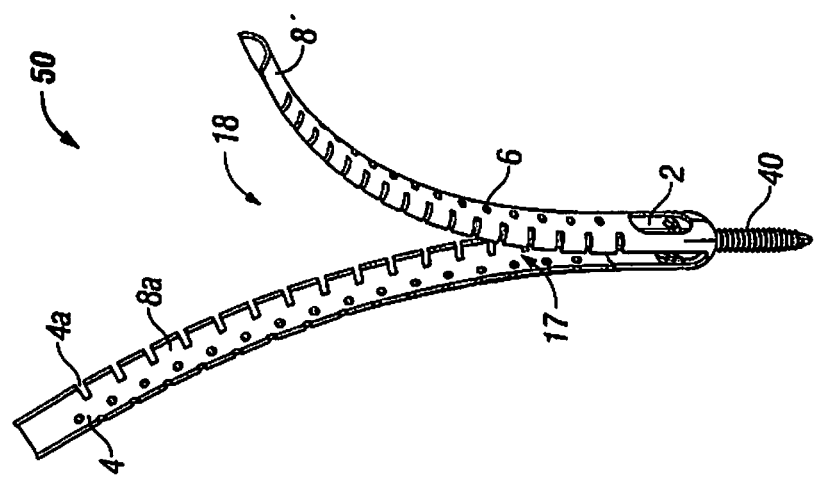
FIG. 8 is a perspective view of a minimally invasive retractor and screw assembly according to a third embodiment of the present disclosure.

Another embodiment of the presently disclosed retractor is illustrated in FIGS. 8 and 9 and shown generally as retractor 50. Retractor 50 is similar to retractor 10, but includes a plurality of living hinges 4 along with their corresponding recesses 4a. Retractor 50 is about 6 inches long and is readily adjusted to a desired length by removing excess material using scissors or a knife. In addition, retractor 50 has an inner diameter that is approximately 16 mm and retractor blades are approximately 1 mm thick. Each living hinge 4 is about 1-2 mm in height and each blade section 8a is about 5 mm. Instrument holes 6 are on 1 cm centerlines. Slot 17 is typically at least 5.5 mm, but will vary according to the size of the rod that will be inserted into the patient. In particular, each retractor blade 8' includes a plurality of blade sections 8a. Each blade section 8a is connected to an adjacent blade section 8a by a living hinge 4. Thus, the plurality of blade sections 8a and living hinges 4 define retractor blade 8'. As in the previous embodiment (FIG. 1), each blade section 8' is substantially parallel to arm 13 to define slot 17 between retractor blades 8'.

When retractor blades 8' are urged radially outward from their initial or rest position towards their retracted position, the size of passage 18 increases. This increase in the size and area of passage 18 improves access to the surgical target site (i.e. near where the retractor is inserted into tissue), thereby increasing visibility of the target site, access for instruments, and access for surgical implants. As shown in FIG. 9, rod 3 is positioned in passage 18 after the surrounding tissue has been retracted using retractor 50. These advantages will be discussed in detail hereinafter. Additionally, the plurality of living hinges 4 greatly increases the adaptability of retractor 50 in comparision to retractor 10. While retractor blades 8 of retractor 10 (FIG. 1) generally bend at its single living hinge 4, the additional living hinges 4 present along retractor blades 8' of retractor 50 permit bending with increased flexibility at a number of positions along the length of each retractor blade 8'. Thus, retractor blades 8' will bend at the living hinge 4 that corresponds to the plane defined by the surface of the patient's body tissue. By using this construction, retractor 50 is usable in patient's having different tissue thicknesses between the vertebral body and the surface of their skin. In addition, since each retractor blade 8' has a plurality of living hinges 4 and blade sections 8a, it is not required for each retractor blade 8' to bend at the same point along the length of retractor 50, thereby accommodating variances in the depth that retractor 50 is inserted. For example, one retractor blade 8' may bend at its fourth living hinge 4, while the other retractor blade 8' may bend at its sixth living hinge 4, thereby accommodating variances in tissue thickness and orientation of retractor 50.

In FIG. 10, a further embodiment of the presently disclosed retractor is illustrated and generally referenced as retractor 60. Retractor 60 is similar to retractor 10 (FIG. 1) with the differences discussed in detail hereinafter. As in the previous embodiment, retractor 60 includes a distal end 14a with a distal region 9a. Distal region 9a includes arms 13a that extend circumferentially and do not form a portion of slot 17 as in the previous embodiment. A living hinge 4' is defined between window 2 and slot 17. In addition, distal region 9a includes slits 16a that are full cuts through the material of distal region 9a defining a plurality of relief regions R'. In this embodiment, relief regions R' are more flexible such that retractor 60 may be separated from a pedicle screw (not shown) and subsequently affixed to the pedicle screw. This configuration permits a surgeon to remove and subcutaneously relocate retractor 60 to gain access to the vertebral disc space. As in the previous embodiments, positioning window 2 distally of slot 17 allows retractor 60 to expand in a medial-lateral orientation such that rod 3 (FIG. 8) may be inserted through passage 18 into the target site.

FIG. 11 illustrates an alternate embodiment of the presently disclosed retractor that is generally referenced as 70. Retractor 70 is substantially similar to the embodiment previously identified as retractor 60 (FIG. 10). However, in this embodiment distal region 9b only includes one arm 13a, thereby increasing the lateral opening near distal end 14b and defining window 2a that is larger than previously disclosed window 2 (FIG. 10). This embodiment provides increased access to the target site, thereby allowing larger implants or instruments to be positioned in the target site.

Another embodiment of the presently disclosed retractor is illustrated in FIG. 12 and referenced as retractor 80. Retractor 80 includes the same or substantially similar components as described hereinabove with respect to retractor 10 (FIG. 1). In this embodiment, retractor 80 includes only one retractor blade 8. This configuration allows greater variability in creating the retracted space as well as increasing access to the target site for using larger instruments or inserting larger devices than possible with retractor 10 (FIG. 1).

It is contemplated that any of the previously disclosed retractors may be formed of a bendable resilient material such that when external spreading forces (i.e. from a Gelpi retractor or the physician's hands) are removed, the retractor blades will return towards their initial position (e.g., substantially parallel to the centerline). It is also contemplated that any of the previously disclosed retractors may be formed of a bendable non-resilient material such that when the external spreading forces are removed, the retractor blades resist returning to their initial position and remain in the retracted position.

Figure 13:
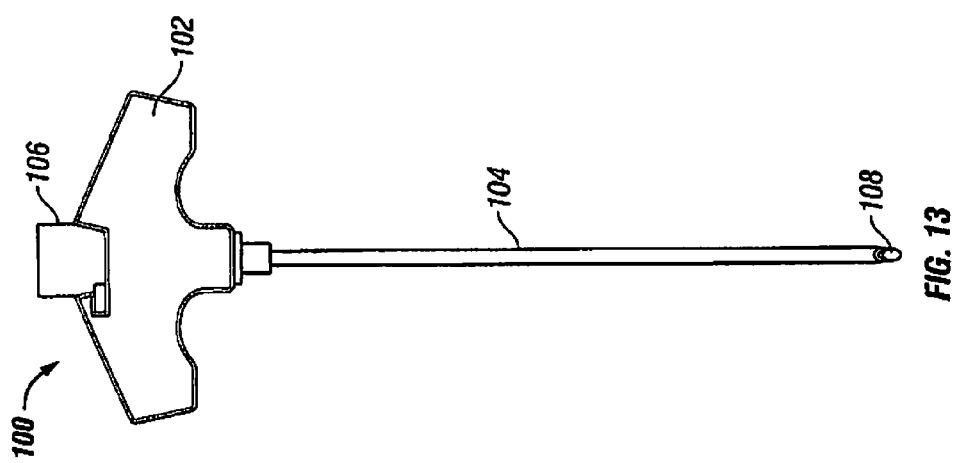
FIG. 13 is a top plan view of bone biopsy needle.
Figure 27:
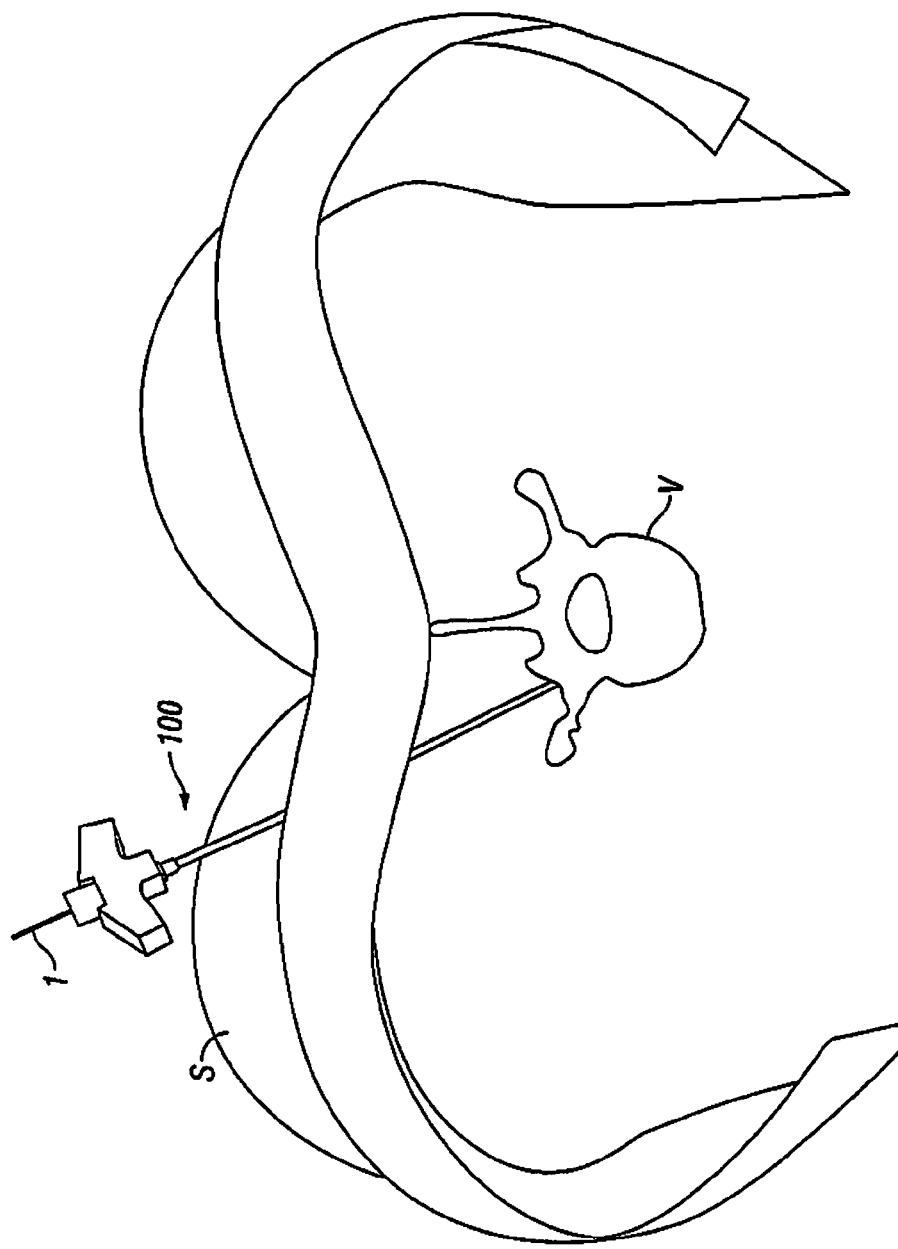
FIG. 27 is a front cross-sectional view of the body of FIG. 26 illustrating insertion of a guide wire through the bone biopsy needle.
Figure 28:
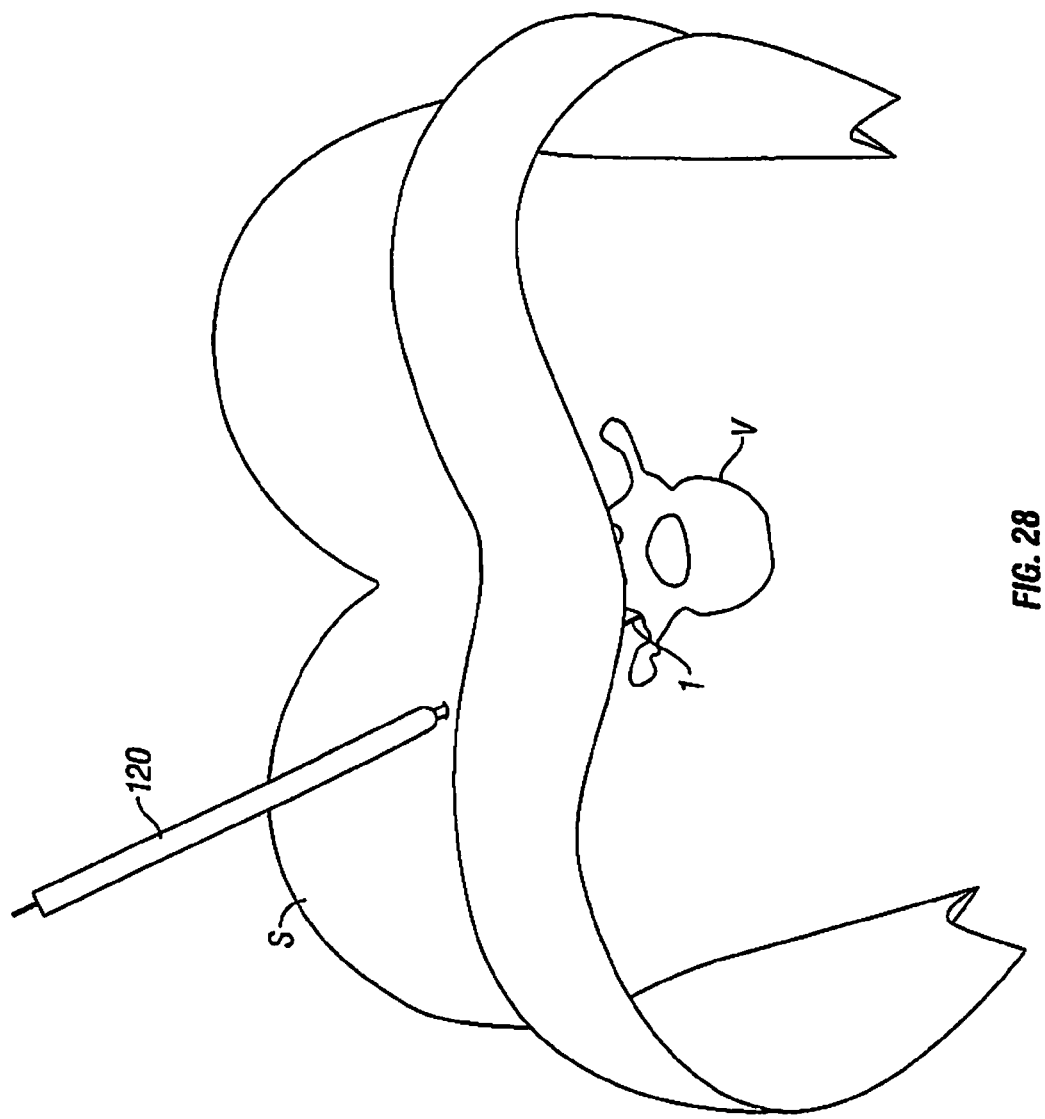
FIG. 28 is a front cross-sectional view of the body of FIG. 27 illustrating tissue separation using the scalpel of FIG. 14.

Other components of the presently disclosed system will now be discussed with reference to FIGS. 13-23. In FIG. 13, a bone biopsy needle (e.g. a Jamshidi needle) 100 is illustrated. Needle 100 includes a handle 102 disposed at a proximal end of needle 100, an elongate tubular member 104 extending distally from handle 102, and a stylet 106. Stylet 106 has a sharpened distal tip 108 that is adapted for penetrating tissue, including bone. In addition, tubular member 104 has a lumen extending from its proximal end to its distal end for receiving stylet 106 therethrough. Stylet 106 is releasably attached to handle 102 such that it may removed once the target site has been pierced by distal tip 108. After stylet 106 is removed, a guidewire 1 (FIG. 27) may be inserted through tubular member 104 and secured or attached at the target site using known techniques.

Figure 14B:
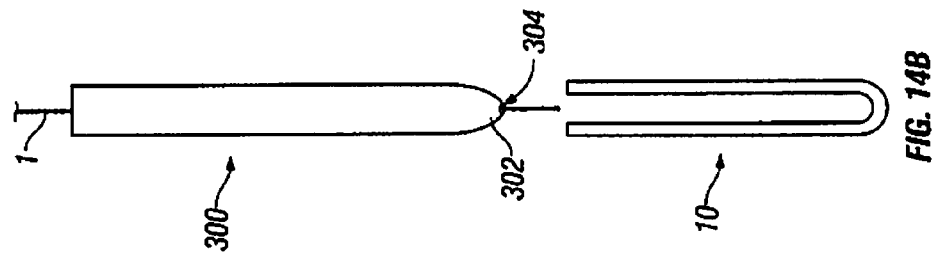
FIG. 14B is a side view of a dilator and retractor.
Figure 14A:
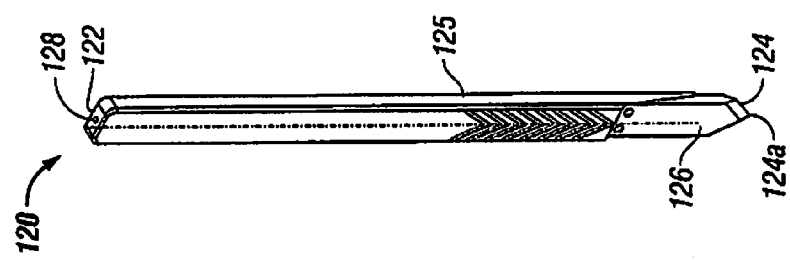
FIG. 14A is a perspective view of a scalpel.

Referring now to FIG. 14, a cannulated scalpel 120 is illustrated. Scalpel 120 includes a housing 125 having a blade 126 disposed therein. Blade 126 has a sharpened distal end 124 for separating tissue. In addition, distal end 124 includes an opening 124a that cooperates with an opening 128 located at proximal end 122 and defines a channel through scalpel 120 for slidably receiving guidewire 1 (FIG. 14A) therethrough.

FIG. 14A shows a dilator 300 configured and dimensioned to be received through a retractor 10 with distal atraumatic blunt tip 302 protruding through opening 7 in retractor 10. Dilator 300 includes a longitudinal passage therethrough having a distal opening 304 for receiving guidewire 1 therethrough. Alternatively, it is contemplated that rather than a retractor, dilator 300 may be used together with a cannula (not shown). Although less desirable, a series of dilators and cannulas can be used.

Figure 29:
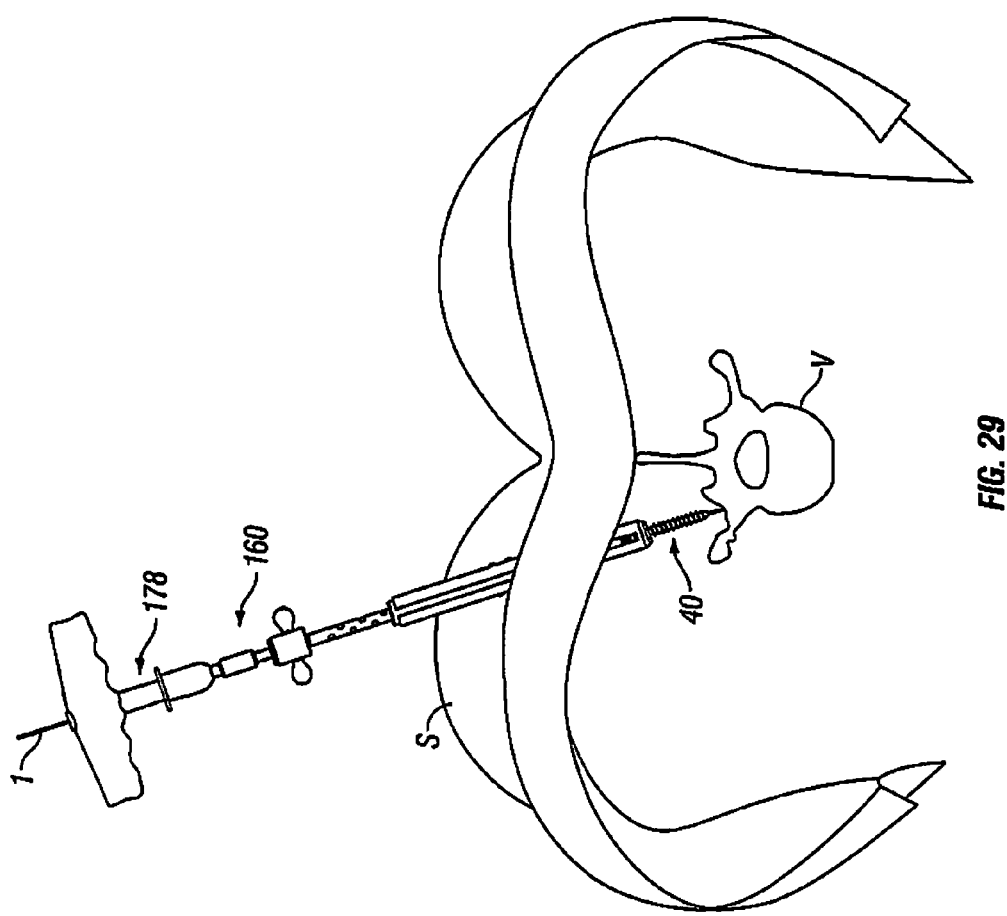
FIG. 29 is a front cross-sectional view of the body of FIG. 27 illustrating insertion of the screw insertion assembly of FIG. 18.

In FIGS. 15-15B, a cannulated bone tap 140 is shown. Bone tap 140 includes an elongated body 142 having a proximal end 146 and a distal end 144. Distal end 144 includes a helical thread 145 for forming threads in a hole that is formed in a bony structure (i.e. a vertebral body). Proximal end 146 includes a tool engagement region 147 that is adapted for cooperating with a driving or rotating tool 178 (FIG. 29) and forming the threads in the bony structure. Driving and rotating tools are well known in the art. In addition, proximal end 146 and distal end 144 cooperate to define a channel 148 extending through bone tap 140 such that bone tap 140 may be slid along guidewire 1. Bone tap 140 is available in a number of different sizes in a range of about 5.5 mm to about 7.5 mm. Alternatively, other bone taps may be used that match the size of the screw threads of the screw that will be implanted into bone.

Figure 17:
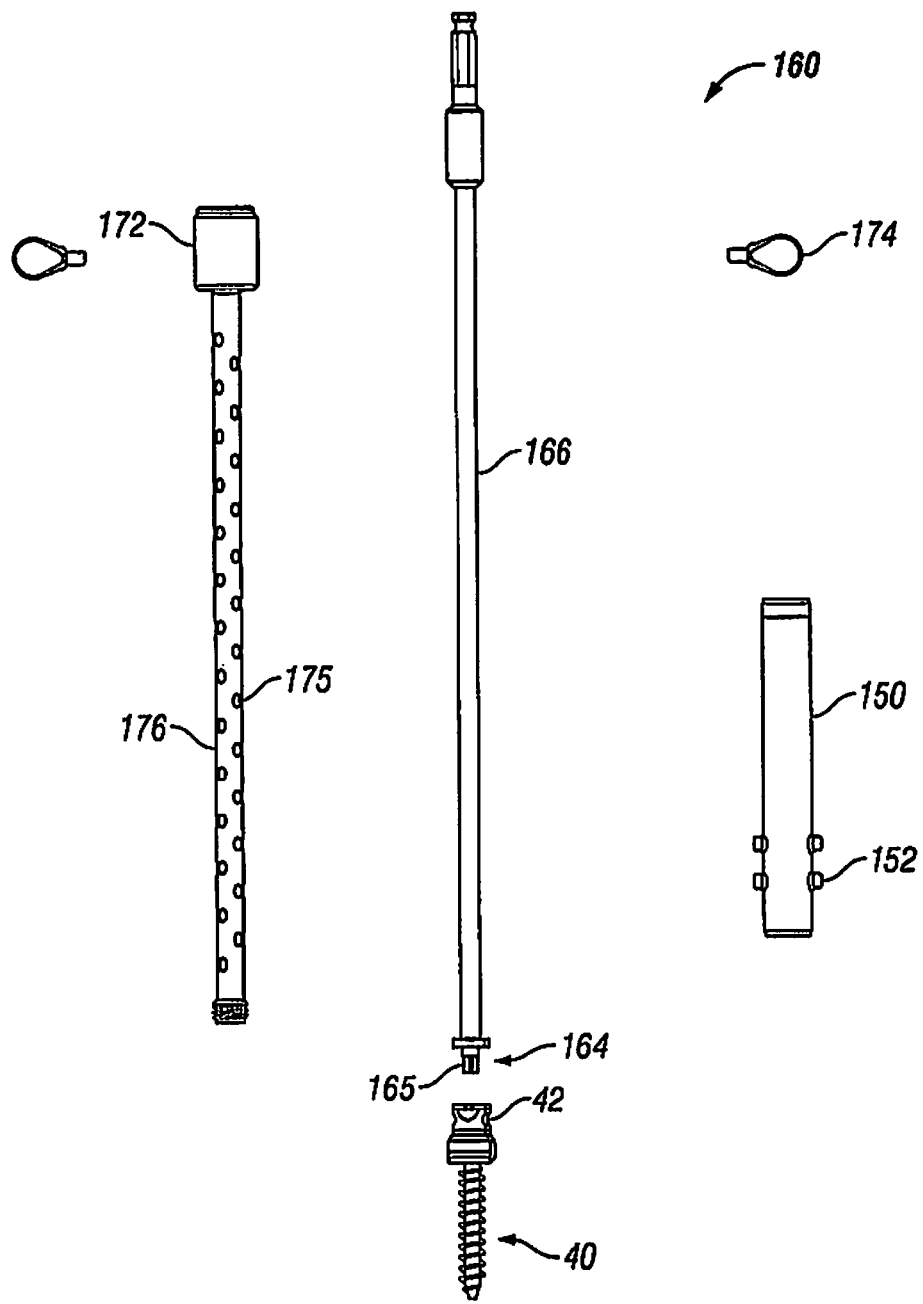
FIG. 17 is an exploded side view of the screw inserter of FIG. 16 shown with a spine screw.

A screw inserter 160 is illustrated in FIGS. 16 and 17. Screw inserter 160 includes an anti-rotation sleeve 150 and a housing 170. Housing 170 includes a body 172 having a pair of handles 174 extending therefrom. Handles 174 facilitate positioning and/or rotating screw inserter 160. A tubular member 176 extends distally from body 172 and includes a plurality of holes 175. A shaft 166 (FIG. 17) is disposed through a lumen of tubular member 176 and is rotatable therein. A tool engaging surface 163 is disposed at a proximal end 162 of shaft 166. At a distal end 164 of shaft 166, a screw engaging structure 165 is disposed that is adapted and configured to releasably engage a head 42 of pedicle screw 40. In particular, screw inserter includes a cross-member 164 and threads 173. During assembly of screw inserter 160 and pedicle screw 40 (FIG. 20), screw engaging structure 165 is inserted into head 42 such that cross-member 163 occupies rod receiving recess 44 and threads 173 engage threaded portion 45 of pedicle screw 40. This arrangement releasably secures pedicle screw 40 to screw inserter 160. When assembled with pedicle screw 40, rotation of shaft 166 also causes rotation of pedicle screw 40 without causing rotation of housing 170. Anti-rotation sleeve 150 is located along an outer surface of tubular member 176 and includes protruding pins or buttons 152.

Figure 18:
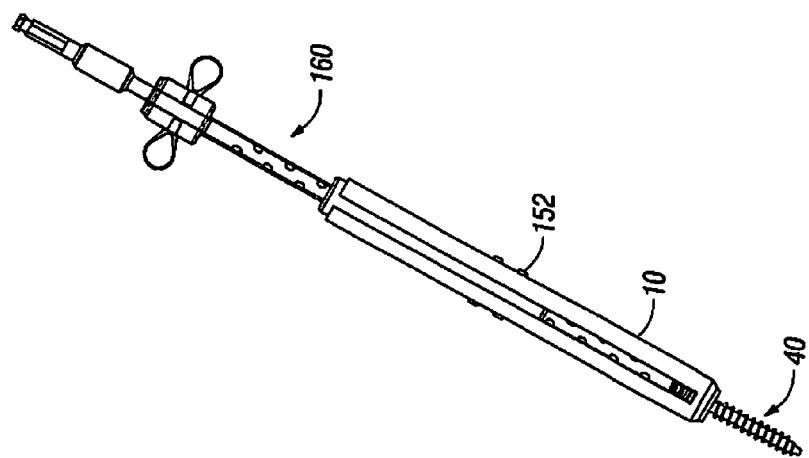
FIG. 18 is a side view of a screw insertion assembly including the screw inserter of FIG. 16, a minimally invasive retractor with a spine screw.

As best seen in FIG. 18, buttons 152 are configured and adapted to releasably engage instrument holes 6 of retractor 10. Although retractor 10 is illustrated in cooperation with screw inserter 160, screw inserter 160 is configured and adapted to cooperate with retractor 50, 60, and 70. Buttons 152 of screw inserter 160 engage instrument holes 6 such that no rotational forces are transferred to the selected retractor while rotating and inserting pedicle screw 40 into a selected vertebral body. This arrangement permits insertion of pedicle screw 40 while minimizing displacement of the selected retractor from its desired location (i.e. target site).

Figure 19:
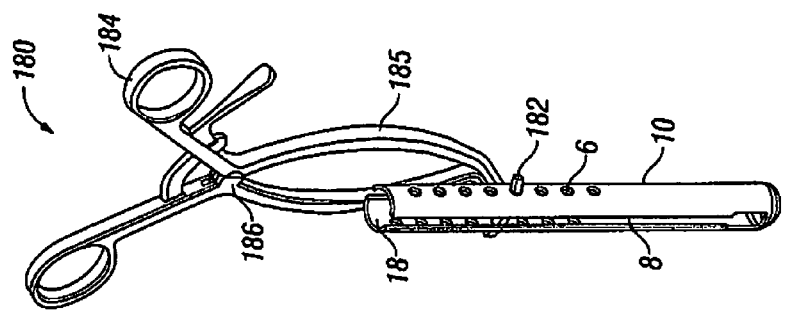
FIG. 19 is a perspective view of a retraction assembly having a minimally invasive retractor and a Gelpi retractor.

A common spreader, or Gelpi retractor 180 is shown in FIG. 19 in cooperation with retractor 10. Gelpi retractor 180 includes a pair of curvate arms 185 that are pivotably connected at pivot point 186. A pair of finger rings 184 are located at a proximal end of Gelpi retractor 180 that permit the physician to selectively move arms 185 towards and away from each other. A finger 182 is located at a distal end of each arm 185 and is configured to releasably engage an instrument hole 6 in retractor 10. As shown, finger rings 184 are laterally offset from arms 185. Thus, pivotable movement of arms 185 urge retractor blades 8 towards and away from each other in response to movement of finger rings 184. Moving finger rings 184 towards each other pivots arms 185 away from each other and urge retractor blades 8 away from each other, thereby enlarging passage 18. Consequently, movement of finger rings 184 away from each other has the opposite effect. Gelpi retractor 180 is also configured and adapted to cooperate with retractor 50, 60, and 70.

Figure 20B:
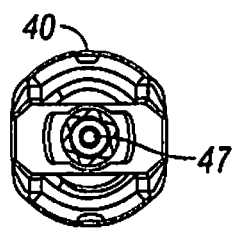
FIG. 20B is top view of the screw of FIG. 20.
Figure 20C:
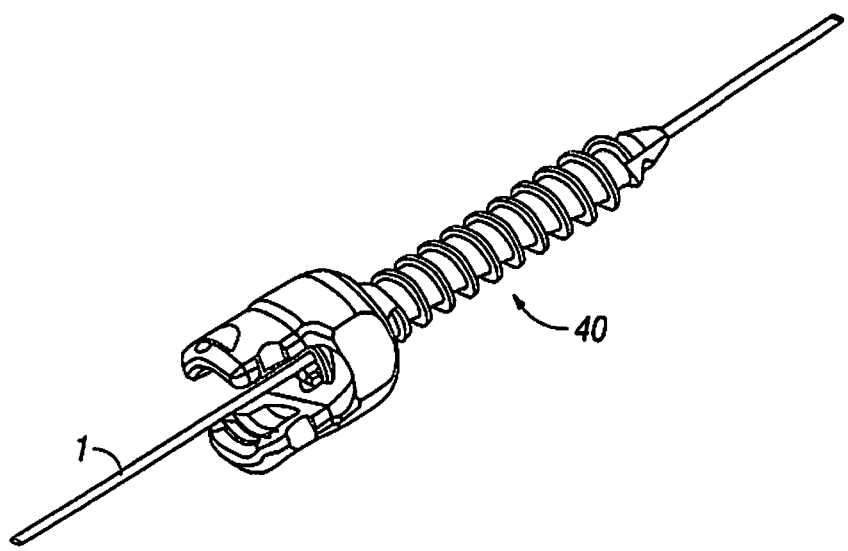
FIG. 20C is a perspective view of the screw of FIG. 20 illustrating an optional guidewire inserted therethrough.

FIGS. 20-20B illustrate a cannulated minimally invasive pedicle screw 40. Pedicle screw 40 includes a helical thread 43 that is sized and configured for insertion into a threaded hole created by bone tap 140. A head 42 includes a tool engaging portion that is adapted to cooperate with screw inserter 160 as previously discussed. A rod receiving passage 44 is formed in head 42. In addition, head 42 includes a threaded portion 45 that is adapted to removably attach to the screw inserter 160 and receive a setscrew (not shown). The setscrew compresses against rod 3 in passage 44 and frictionally engages rod 3 to hold it in a desired position. Setscrews are well known in the art. A throughbore 47 extends between a proximal end and a distal end of pedicle screw 40 for receiving guidewire 1 therethrough (FIG. 20B).

Figure 21:
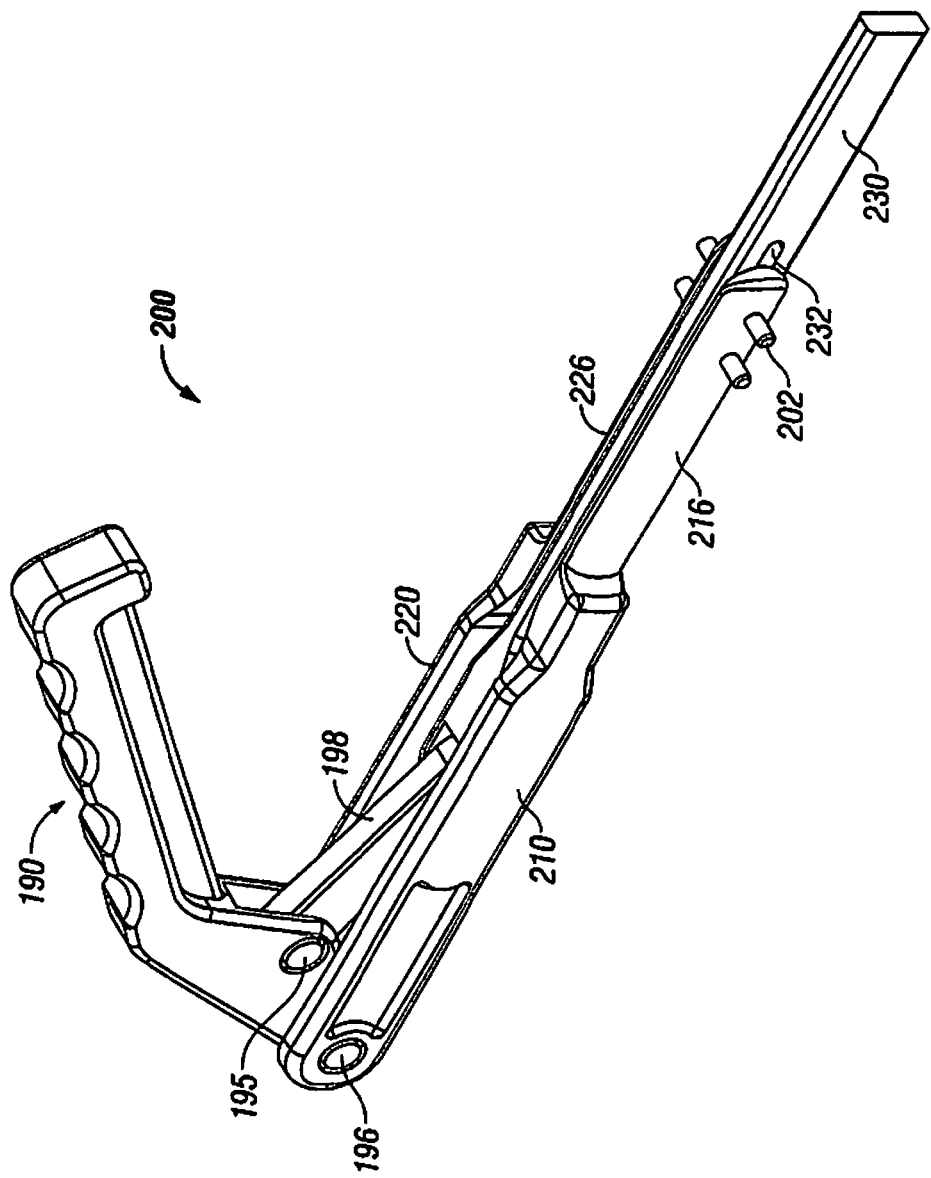
FIG. 21 is a perspective view of a retractor extractor instrument according to an embodiment of the present disclosure.
Figure 22:
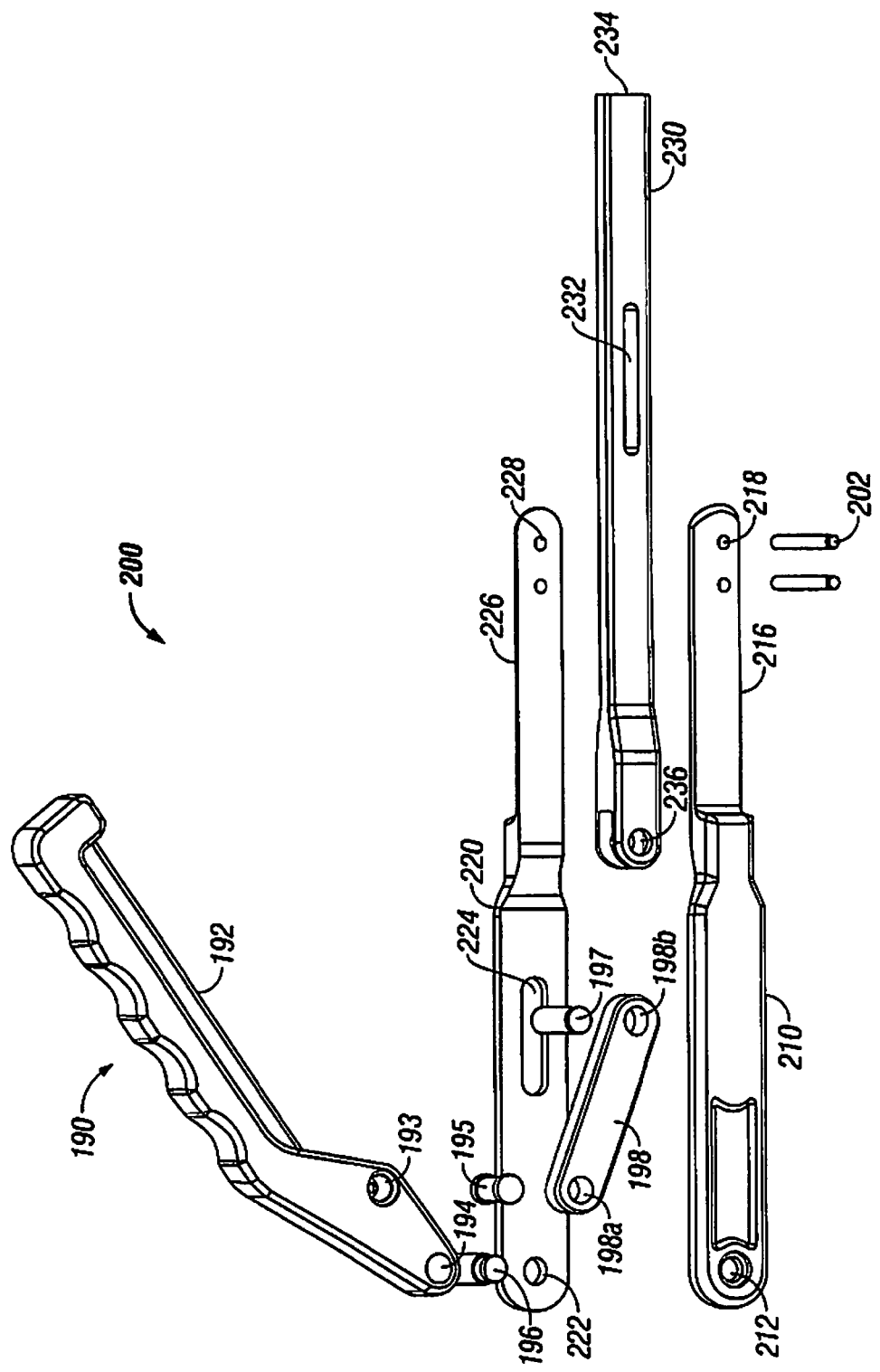
FIG. 22 is an exploded perspective view of the retractor extractor instrument of FIG. 18.
Figure 23:
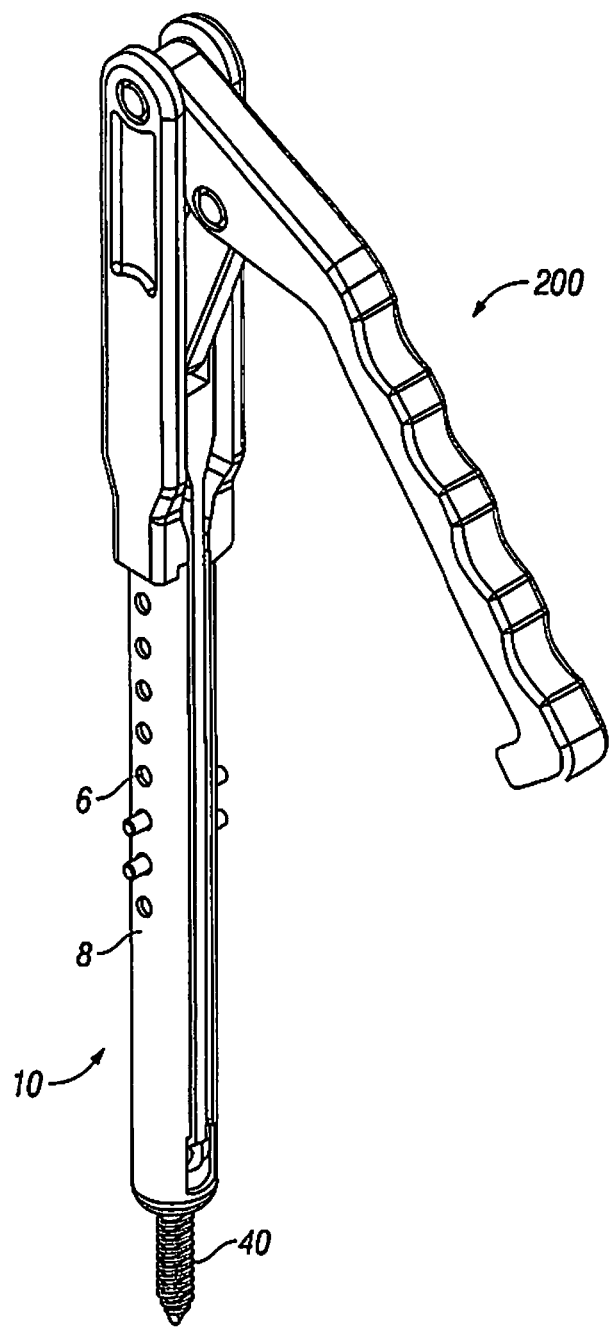
FIG. 23 is a perspective view of the retractor extractor instrument of FIG. 21 coupled to a minimally invasive retractor which is associated with a spine screw.

A retractor extractor instrument 200 is illustrated in FIGS. 21-23. Retractor extractor 200 includes handle portion 190, arms 210 and 220, and extractor bar 230. Handle portion 190 includes a handle grip 192 having openings 193, 194 disposed at one end thereof. Pin 196 extends through opening 194 and pivotably couples handle portion 190 to arms 210, 220 by extending through holes 212, 222 of arms 210, 220. A pin 195 extends through opening 193 and pivotably couples handle portion 190 to pivot bar 198 through hole 198a. At an opposing end of pivot bar 198, hole 198b receives a pin 197. Pin 197 extends between arms 210, 220 and is slidably captured therebetween. In particular, pin 197 slides proximally and distally within a recess 224 of arm 220. Arm 210 has an identical recess that is not shown. Additionally, pin 197 extends through an opening 236 of extractor bar 230. Retractor bar has a slot 230 that extends parallel to its longitudinal axis and slidably receives posts 202 therethrough. Posts 202 are attached to blade portions 216, 226 through openings 218, 228. Additionally, posts 202 are adapted to releasably engage instrument holes 6 of the previously disclosed retractors (FIG. 23). At a distal end of extractor bar 230, a blunt end 234 is located for bluntly engaging head 42 of pedicle screw 40 or a rod disposed therein.

Pivoting handle grip 192 towards arms 210, 220 simulataneously moves extractor bar 230 distally (i.e. towards the screw) such that pins 202 on arms 210, 220 and distal blunt end 234 move apart relative to each other. This simultaneous relative movement between extractor bar 230 and pins 202 causes the retractor to separate from the pedicle screw at the relief regions without applying any appreciable downward forces on the implant or the patient.

Figure 24:
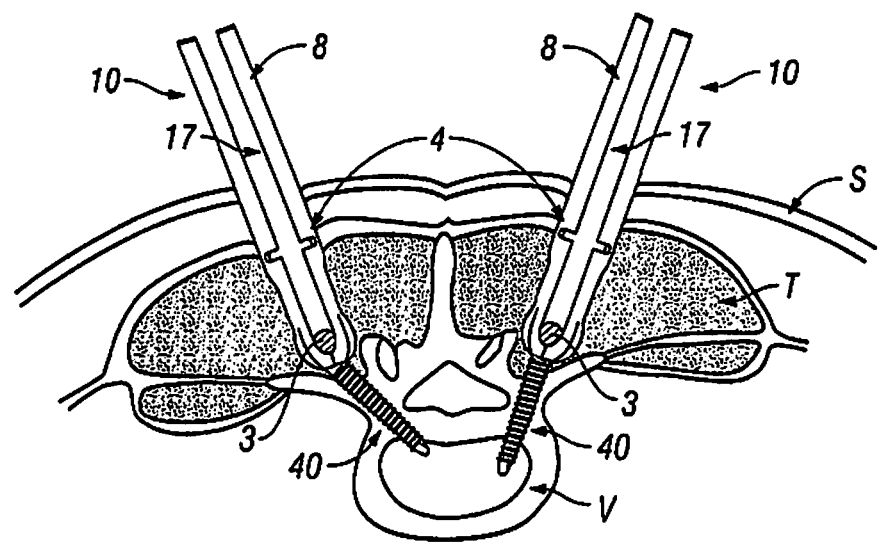
FIG. 24 is a front cross-sectional view of a vertebral body with a pair of minimally invasive retractors attached using screws with the blades in their initial position and rods positioned in the passages of the minimally invasive retractors.
Figure 25:
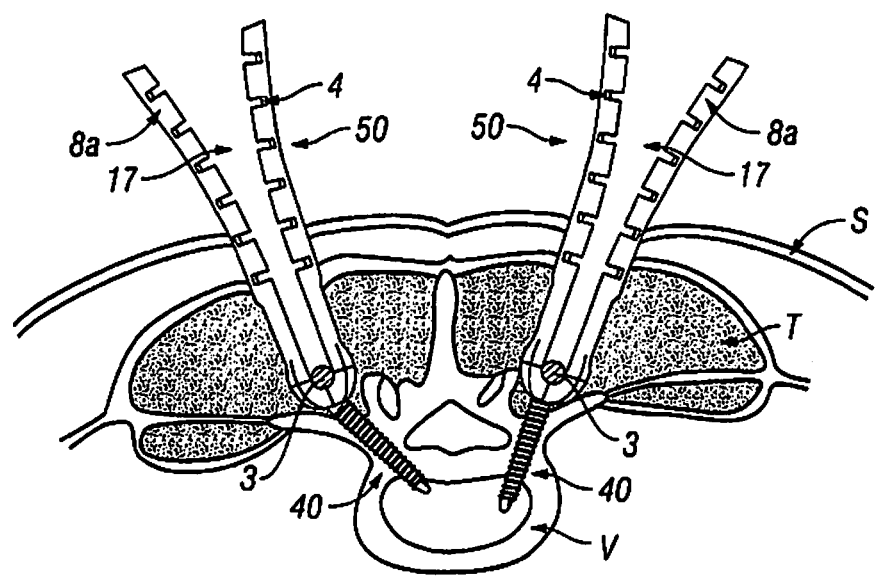
FIG. 25 is a front cross-sectional view of the vertebral body with a pair of minimally invasive retractors attached using screws after retracting tissue with rods positioned in the passages of the minimally invasive retractors.
Figure 26:
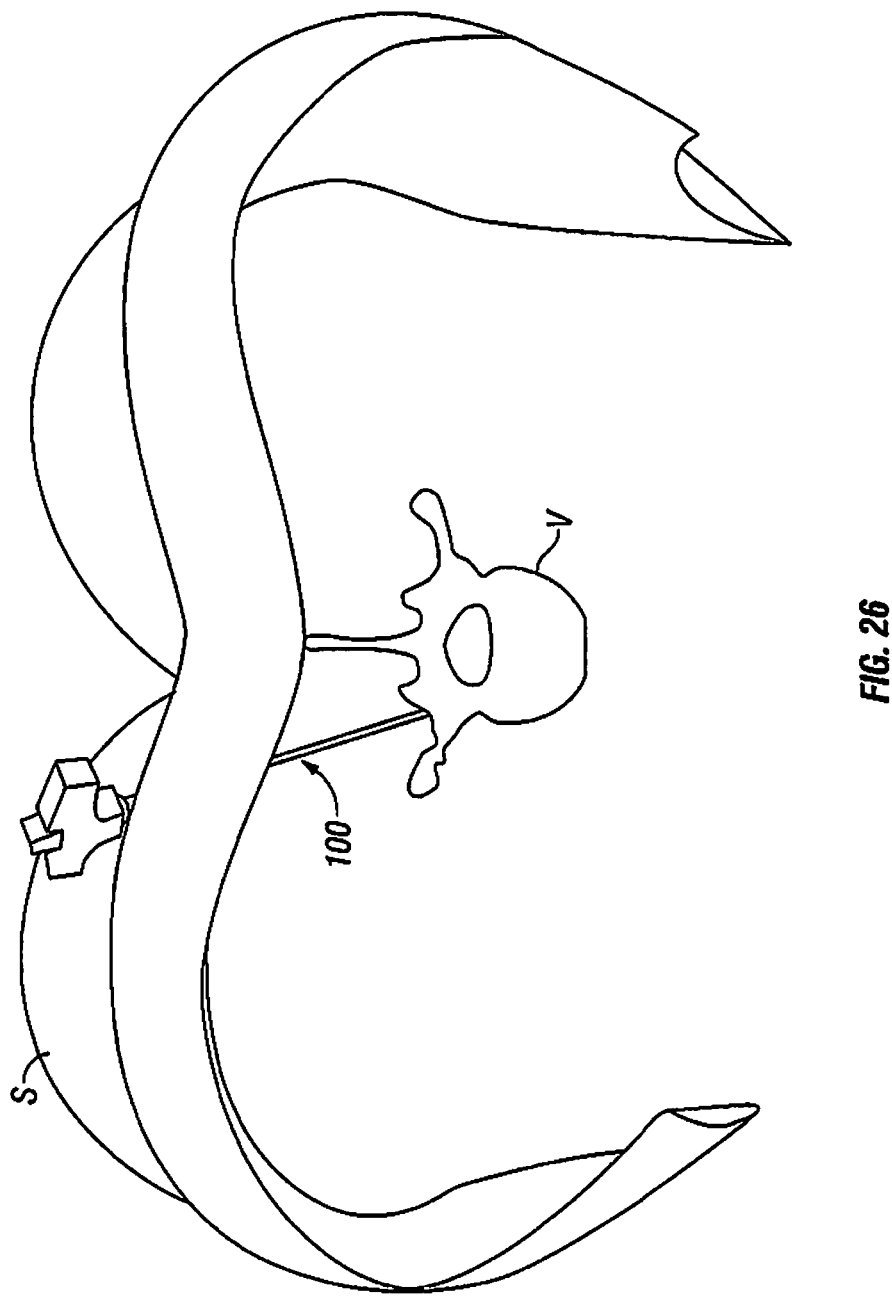
FIG. 26 is a front cross-sectional view of a body illustrating insertion of the bone biopsy needle of FIG. 13 into a vertebral body.

Use of the presently disclosed system will now be described with reference to FIGS. 24-30. In a first method, retractor 10 is assembled with pedicle screw 40 as shown in FIG. 24. The assembled apparatus is inserted into an incision through the patient's skin S and muscle/fat tissue T such that pedicle screw 40 is subsequently threaded into a vertebral body V. Once the desired number of retractors 10 are affixed to vertebral body V, retractor blades 8 are spread apart to retract skin S and tissue T to create a retracted area at the target site. Alternatively, retractor 50 may be assembled with pedicle screw 40 to retract tissue as shown in FIG. 25. In either method, rod 3 is inserted in passage 18 when passage 18 is in an expanded state (i.e. tissue has been retracted). Additionally, rod 3 is repositioned through passage 18 and subcutaneously such that is may be secured to fastening regions of pedicle screws in adjacent vertebral bodies.

Turning now to FIGS. 26-30, an alternate technique is illustrated. Biopsy needle 100 is inserted through skin S of the patient until its distal end contacts the selected point on vertebral body V. Biopsy needle 100 may be inserted in a known manner, such as percutaneously under fluoroscopic imaging, or under optical or magnetic image guidance (such as the STEALTH® system available from Medtronic Sofamor Danek). A small puncture in the vertebral body V is made using sharpened distal tip 108 (FIG. 13). After pin 106 is removed from biopsy needle 100, guidewire 1 is inserted through biopsy needle 100 and affixed to vertebral body V. Guidewire 1 now is in position to direct further instruments and devices to the selected location on vertebral body V. Alternately, guidewire 1 may be insterted into vertebral body V without first using biopsy needle 100. The size of the working area may be increased at the physician's discretion. In instances where it is desired to increase the working area, the physician may use scalpel 120 along guidewire 1 (FIG. 28) to dissect additional tissue. In order to permit inspection of the position of guidewire 1 prior to insertion of a spine screw, a dilator 300 and optional retractor 10 may be inserted over the guidewire by inserting guidewire 1 through dilator opening 304 (FIG. 14A) with the dilator inserted through retractor 10. Once the dilator tip with retractor is inserted to the target site, the dilator may be removed and placement of the guidewire may be inspected through the retractor. If the surgeon is satisfied with the placement of guidewire 1, then the procedure may continue through the retractor or the retractor may be removed and another inserted with a screw. If, on the other hand, the surgeon desires to change the guidewire location, another guidewire may be placed through the retractor, such as by inserting bone biopsy needle 100 through the retractor to a different placement in the bone and inserting a new guidewire at the new location. The former guidewire may then be removed. If desired, the physician may pre-drill a threaded bore in vertebral body V using bone tap 140 inserted along guidewire 1 to prepare the bore.

Figure 30:
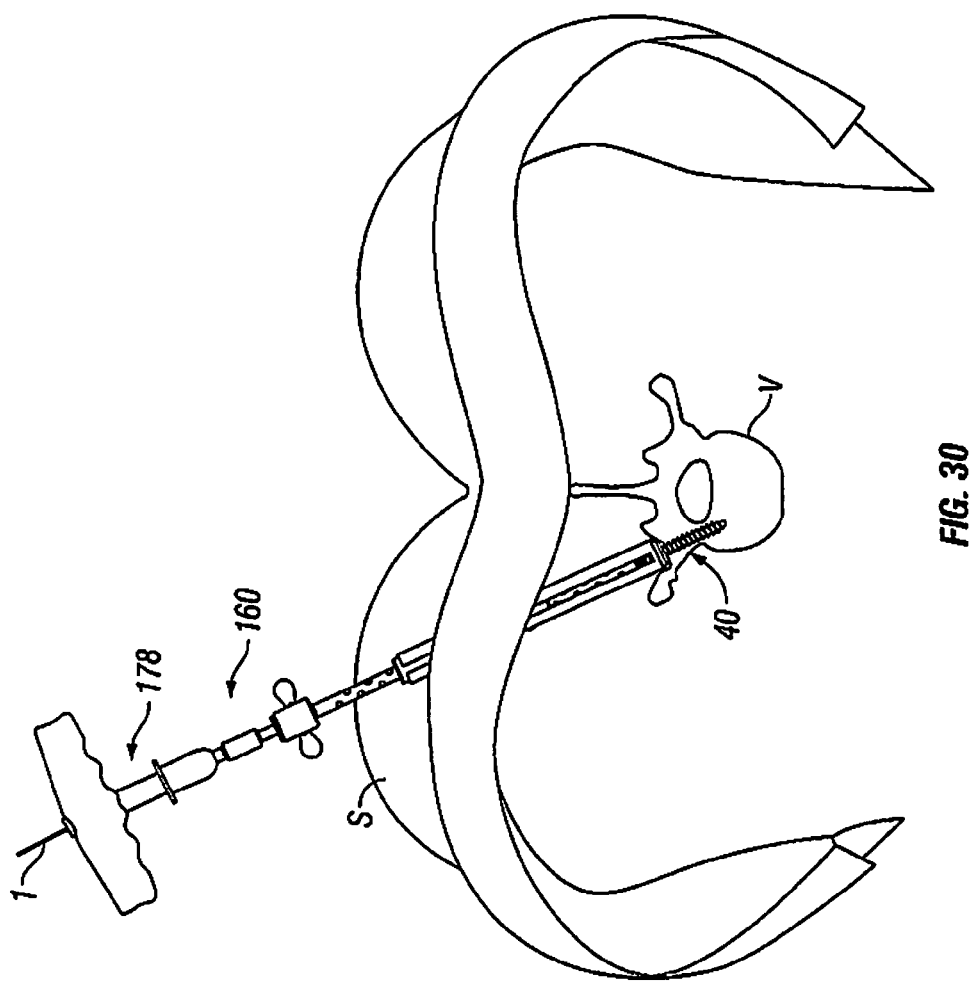
FIG. 30 is a front cross-sectional view of the body of FIG. 29 with the vertebral body shown in a cross-sectional view and illustrating attachment of the screw of the screw insertion assembly to the vertebral body.

Once the target site is ready to accept a pedicle screw and retractor, an assembly including pedicle screw 40, retractor 10, and screw inserter 160 is slid along guidewire 1 to reach the target site. Using optional driving handle 178 (FIG. 29), the physician rotates screw inserter 160 to drive pedicle screw 40 into vertebral body V (FIG. 30). After pedicle screw 40 is secured in vertebral body V, screw inserter 160 is removed and retractor 10 remains in place secured by the screw which has been inserted into bone. This technique is also adapted for use with retractor 50. The finished result of the attached retractors is the same as shown in FIGS. 24 and 25.

Retractor blades 8 are spread apart to retract tissue in the working area. As previously discussed, retractor blades 8 may be spread apart using Gelpi retractor 180 (FIG. 19) or by the physician manually grasping retractor blades 8 to urge them apart. After the desired retraction is achieved, rod 3 is inserted through passage 18 of retractor 10, 50 and is guided through window 2.

It has been found that a rod of sufficient length for a multiple level implant construct may be inserted subcutaneously so that the rod is aligned with and inserted into a plurality of screw heads. This technique may be particularly useful in so-called 360 degree procedures where an interbody implant is inserted using an anterior approach and a screw-rod construct is inserted using a posterior approach. Alternatively, the surgeon may selectively make an incision between adjacent retractors. The latter approach permits a rod to be inserted through the incision to adjacent screws. Once rod 3 is positioned between pairs of pedicle screws 40 and, in particularly through the respective rod receiving passages 44, rod 3 is secured in place using setscrews as previously discussed.

Once the screw-rod construct is complete, retractors 10, 50 are removed from the patient using retractor extractor 200. Retractor extractor 200 is positioned atop pedicle screw 40 such that distal end 234 of extractor bar 230 (FIG. 23) rests flush against the set screw installed in head 42 of pedicle screw 40 or rests upon the rod installed in an alternate pedicle screw. The physician repositions retractor blades 8 towards arm blades 216, 226 (FIG. 22) of retractor extractor 200 such that posts 202 engage instrument holes 6. Once retractor extractor 200 is installed, the physician pivots handle grip 192 towards arms 210, 220. This pivotable movement drives extractor bar 230 distally against head 42 while simultaneously pulling retractor blades 8 proximally such that relief regions R (FIG. 1) separate from each other along slits 16. As such, retractor 10, 50 is separated from pedicle screw 40 without imparting significant downward or rotational forces against the patient's body. Retractor 10, 50 may now be removed from the patient and this process may be repeated for each installed retractor.

In an alternate procedure, the physician first prepares the surgical site including positioning a guidewire as discussed hereinabove, optionally using scalpel 120 to prepare an incision, and inserting one of the previously disclosed retractors without a pedicle screw. Once the selected retractor is positioned in a desired location, the physician retracts the surrounding tissue as discussed hereinabove. Subsequently, the physician attaches pedicle screw 40 to the vertebral body V using screw inserter 160. In this method, the selected retractor is already in position prior to attaching pedicle screw 40 to vertebral body V. In particular, the physician assembles pedicle screw 40 and screw inserter 160. Once assembled, the screw insertion assembly is inserted into passage 18 of the retractor and pedicle screw 40 is rotated such that it bores into vertebral body V and head 42 seats on the interior surface of the distal region of the retractor and thus attaches the retractor to vertebral body V. Optionally, the physician may use cannulated bone tap 140 to prepare the bore.

In the disclosed embodiments, each retractor is utilized, but not limited to, a method whereby an initial incision is made in the skin of approximately 10-15 mm in length. Surgeon preference will dictate the need for one or more stages of dilators to aid in expanding the wound before introducing one or more retractors in combination with pedicle screws. Normal surgical techniques may be used to close the incision(s).

In the disclosed embodiments, the retractor may be manufactured from medical grade plastic or metal, thermoplastics, composites of plastic and metal, or biocompatible materials. A plastic part is made from, but not limited to, polypropylene and polyethylene. Plastic parts may be transparent or opaque and may have radio opaque markers for visibility during various imaging techniques. A metallic part utilizes such materials as, but not limited to, aluminum, stainless steel, and titanium. In addition, the parts may have a reflective or non-reflective coating to aid in increasing visibility in the wound and may have an artificial lighting feature.

The disclosed retractors, as with any surgical instrument and implant, must have the ability to be sterilized using known materials and techniques. Parts may be sterile packed by the manufacturer or sterilized on site by the user. Sterile packed parts may be individually packed or packed in any desirable quantity. For example, a sterile package may contain one or a plurality of retractors in a sterile enclosure. Alternatively, such a sterile surgical kit may also include one or a plurality of bone biopsy needles (FIG. 13), guide wires (FIG. 20B), sterile cannulated scalpels (FIG. 14), or dilators (FIG. 14A).

It will be understood that various modifications may be made to the embodiments of the presently disclosed retraction system. Therefore, the above description should not be construed as limiting, but merely as exemplifications of embodiments. Those skilled in the art will envision other modifications within the scope and spirit of the present disclosure.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

What is claimed is:

1. A surgical retractor comprising:
   an elongate member;
   a coupling region disposed at a distal end of the surgical retractor, the coupling region including an opening at a distal end thereof and at least one relief region configured to permit the retractor to separate from a head of a bone screw upon application of a predetermined force to disengage the refractor from the head of the bone screw; and
   a flexible joint coupling the elongate member to the coupling region, wherein the elongate member is bendable radially outwards in response to applied forces to retract surrounding tissue, and the elongate member is rotatable relative to the bone screw when the elongate member is coupled to the bone screw.

2. The surgical retractor according to claim 1, wherein the at least one relief region is defined by at least one slit extending proximally from the opening.

3. The surgical retractor according to claim 1, wherein the opening has a diameter larger than a diameter of a shank of the bone screw and smaller than a diameter of the head of the bone screw.

4. The surgical retractor according to claim 1, wherein the flexible joint is a living hinge.

5. The surgical retractor according to claim 4, wherein the flexible joint defines a recess defining the living hinge.

6. The surgical retractor according to claim 4, further comprising a plurality of living hinges along a length of the retractor.

7. The surgical retractor according to claim 1, wherein the distal end of the retractor has an interior surface having a generally concave spherical geometry that is adapted to mate with the head of the bone screw.

8. The surgical retractor according to claim 1, wherein the distal end of the retractor has an outer surface having a generally convex geometry that facilitates insertion of the retractor through layers of body tissue.

9. The surgical retractor according to claim 1, wherein the elongate member includes a pair of retractor blades transitionable between a first state in which the pair of retractor blades are substantially parallel to each other and a second state in which the pair of retractor blades define a substantially V-shaped configuration.

10. The surgical retractor according to claim 9, wherein the pair of retractor blades has a plurality of instrument holes disposed thereon.

11. The surgical retractor according to claim 9, wherein each retractor blade has a generally arcuate structure in cross-section taken across a length of the elongate member.

12. The surgical retractor according to claim 11, wherein each retractor blade has an arcuate configuration that is less than about 180 degrees.

13. The surgical retractor according to claim 1, wherein the retractor defines a passage that extends substantially along the entire length of the retractor.

14. The surgical retractor according to claim 13, wherein the passage is configured and dimensioned to receive a dilator therethrough.

15. The surgical retractor according to claim 1, wherein the retractor is formed of a bendable resilient material.

16. The surgical retractor according to claim 1, wherein the retractor is formed of a bendable non-resilient material.

17. The surgical retractor according to claim 1, wherein the at least one relief region is configured to permit the retractor to separate from the head of the bone screw upon application of a longitudinal force to disengage the retractor from the head of the bone screw.

18. A surgical retractor comprising:
    an elongate member;
    a coupling region disposed at a distal end of the surgical retractor, the coupling region including an opening at a distal end thereof and at least one relief region configured to permit the retractor to separate from a head of a bone screw upon application of a longitudinal force to disengage the refractor from the head of the bone screw; and
    a flexible joint coupling the elongate member to the coupling region, wherein the elongate member is bendable radially outwards in response to applied forces to retract surrounding tissue.

19. The surgical retractor according to claim 18, wherein the elongate member is rotatable relative to the bone screw when the elongate member is coupled to the bone screw.

20. The surgical retractor according to claim 18, wherein the at least one relief region is defined by at least one slit extending proximally from the opening.

21. The surgical retractor according to claim 18, wherein the distal end of the retractor has an interior surface having a generally concave spherical geometry that is adapted to mate with the head of the bone screw.

22. The surgical retractor according to claim 18, wherein the distal end of the retractor has an outer surface having a generally convex geometry that facilitates insertion of the retractor through layers of body tissue.

23. The surgical retractor according to claim 18, wherein the elongate member includes a pair of retractor blades transitionable between a first state in which the pair of retractor blades are substantially parallel to each other and a second state in which the pair of retractor blades define a substantially V-shaped configuration.

24. The surgical retractor according to claim 18, wherein the retractor defines a passage that extends substantially along an entire length of the refractor.

* * * * *